US012805787B2

(12) United States Patent

Berdonini et al.

(10) Patent No.: US 12,805,787 B2
(45) Date of Patent: Nov. 24, 2026

(54) INTEGRATED ELECTRONIC CIRCUIT WITH OFFSET COMPENSATION FOR AN IMPLANTABLE PROBE

(71) Applicant: FONDAZIONE ISTITUTO ITALIANO DI TECNOLOGIA, Genoa (IT)

(72) Inventors: Luca Berdonini, Genoa (IT); Gian Nicola Angotzi, Genoa (IT); Fabio Boi, Genoa (IT); Joao Filipe Rodrigues Ribeiro, Genoa (IT)

(73) Assignee: FONDAZIONE ISTITUTO ITALIANO DI TECNOLOGIA (IT)

(*) Notice: Subject to any disclaimer, the term of this patent is extended or adjusted under 35 U.S.C. 154(b) by 270 days.

(21) Appl. No.: 18/705,032

(22) PCT Filed: Nov. 2, 2022

(86) PCT No.: PCT/IB2022/060551
§ 371 (c)(1),
(2) Date: Apr. 26, 2024

(87) PCT Pub. No.: WO2023/079452
PCT Pub. Date: May 11, 2023

(65) Prior Publication Data

US 2025/0000418 A1 Jan. 2, 2025

(30) Foreign Application Priority Data

Nov. 3, 2021 (IT) ........................ 102021000027956

(51) Int. Cl.
*A61B 5/277* (2021.01)
*A61B 5/293* (2021.01)
(Continued)

(52) U.S. Cl.
CPC .............. *A61B 5/277* (2021.01); *A61B 5/293* (2021.01); *A61B 5/302* (2021.01); *A61B 5/304* (2021.01)

(58) Field of Classification Search
CPC ......... A61B 5/277; A61B 5/293; A61B 5/302; A61B 5/304
See application file for complete search history.

(56) References Cited

U.S. PATENT DOCUMENTS

2018/0078194 A1* 3/2018 Han ....................... A61B 5/294
2023/0389877 A1* 12/2023 Wendler ................. A61B 5/685

OTHER PUBLICATIONS

International Search Report and Written Opinion corresponding to International Patent Application No. PCT/IB2022/060551, mailed Feb. 16, 2023.

(Continued)

*Primary Examiner* — Bradford C. Blaise
(74) *Attorney, Agent, or Firm* — McAndrews, Held & Malloy, Ltd.

(57) ABSTRACT

Integrated electronic circuit (10,12) for an implantable probe module, including a number of pixel circuits each having: an electrode for contacting a biological tissue; a biasing stage ($M_1$,C) with a capacitor and a first transistor, which is coupled to the capacitor and injects in an input node ($N_{IN}$) a biasing current ($I_{bias}$) that depends upon the charge of the capacitor; a second transistor coupled to the electrode and to the input node ($N_{IN}$); an amplifier coupled to a reference voltage ($V_{ref1}$) and to the input node ($N_{IN}$). The integrated electronic circuit (10,12) furthermore includes a feedback stage electrically controllable so as to be alternatively coupled or decoupled from each pixel circuit. The feedback stage forms, when coupled to a pixel circuit, an autozeroing loop that charges the corresponding capacitor so that the biasing current ($I_{bias}$) is such that on the input node ($N_{IN}$) a (Continued)

voltage substantially equal to the reference voltage is present.

9 Claims, 7 Drawing Sheets

(51) Int. Cl.
*A61B 5/302* (2021.01)
*A61B 5/304* (2021.01)

(56) References Cited

OTHER PUBLICATIONS

Imfeld K et al, "Large-Scale, High-Resolution Data Acquisition System for Extracellular Recording of Electrophysiological Activity", IEEE Transactions on Biomedical Engineering, IEEE, USA, vol. 55, No. 8, Aug. 1, 2008 (Aug. 1, 2008), p. 2064-2073, XP011247745.
Angotzi G N et al, "A low-power, low-area modular architecture for high density neural probes", 2015 7th International IEEE/EMBS Conference on Neural Engineering (NER), IEEE,Apr. 22, 2015 (Apr. 22, 2015), p. 521-524, XP033166272.

* cited by examiner

INTEGRATED ELECTRONIC CIRCUIT WITH OFFSET COMPENSATION FOR AN IMPLANTABLE PROBE

CROSS-REFERENCE TO RELATED APPLICATIONS

The present application is filed pursuant to 35 U.S.C. 371 as a U.S. National Phase application of International Patent Application No. PCT/IB2022/060551, which was filed Nov. 2, 2022, claiming priority from Italian patent application no. 102021000027956 filed on Nov. 3, 2021 the entire disclosure of each is incorporated herein by reference.

TECHNICAL FIELD

The present invention refers to an integrated electronic circuit with offset compensation for an implantable probe.

BACKGROUND

As is well known, so-called implantable multi-electrode array probes that are adapted to record numerous (in the order of thousands) electrophysiological signals generated, for example, by individual neurons are nowadays available.

In particular, active type probes are known, which each include a plurality of pixels, each of which integrates a respective sensing electrode and a corresponding amplification circuitry.

In use, the sensing electrode is contacted with a corresponding portion of tissue (e.g., brain tissue), in order to acquire a corresponding initial electrical signal, which is then amplified by the corresponding amplification circuitry, so as to generate a corresponding output signal.

For example, FIG. 1 shows a probe 1, which comprises a plurality of pixels 2 and a shared circuitry 4, which is electrically coupled to the pixels 2 (for example, is integrated in the same plate) and is configured so as to allow the parallel acquisition of the output signals generated by the pixels 2, for example by implementing a multiplexing mechanism over time, that is, so as to query each pixel 2 in a corresponding time interval.

In order to have a high density of pixels 2 per unit area, each pixel 2, and therefore also the corresponding amplification circuitry, should occupy a reduced area. For this reason, it is known to use the so-called CMOS technology to create pixels 2, this technology also allowing to reduce consumptions.

However, the Applicant has observed how, in use, a corresponding electrode-electrolyte interface is formed at each sensing electrode and which is subject to high direct voltage variations, i.e. it exhibits a DC offset that can be particularly high (up to hundreds of millivolts). The causes of this DC offset may include, for example, the differences in composition of the biological tissue being measured.

In order to reduce the impact of the aforementioned DC offset on the output signal, it is for example possible to implement an AC coupling between the amplification circuitries and the sensing electrodes, however this solution requires the formation of capacitors with high capacitance, resulting in high area occupancy. This solution is therefore unsuitable for high channel density recording systems, i.e. for recording systems having a high number of pixels per unit area.

The article "Large scale, high-resolution data acquisition system for extracellular recording of electrophysiological activity", by Imfeld K. et al., IEEE TRANSACTIONS ON BIOMEDICAL ENGINEERING, vol. 5, no. 8, pp. 2064-2073 and the article "A low-power, low-area modular architecture for high-density neural probes", by Angotzi G. N. and Berdondini L., 7th Annual International IEEE EMBS Conference on Neural Engineering, Montpellier, France, 20-22 Apr. 2015 describe electronic circuits in which an electrode is polarised by means of a pair of P-MOS transistors connected in parallel, which together deliver a current that polarises a further P-MOS transistor, whose gate terminal is connected to the electrode.

SUMMARY

Aim of the present invention is therefore to provide an integrated electronic circuit that allows to solve at least in part the drawbacks of the prior art.

According to the invention, there is provided an integrated electronic circuit as defined in the appended claims.

BRIEF DESCRIPTION OF THE FIGURES

For a better understanding of the invention, embodiments thereof will now be disclosed, for merely illustrative and non-limiting purposes and with reference to the enclosed drawings, wherein.

DESCRIPTION OF EMBODIMENTS

Figure 1:
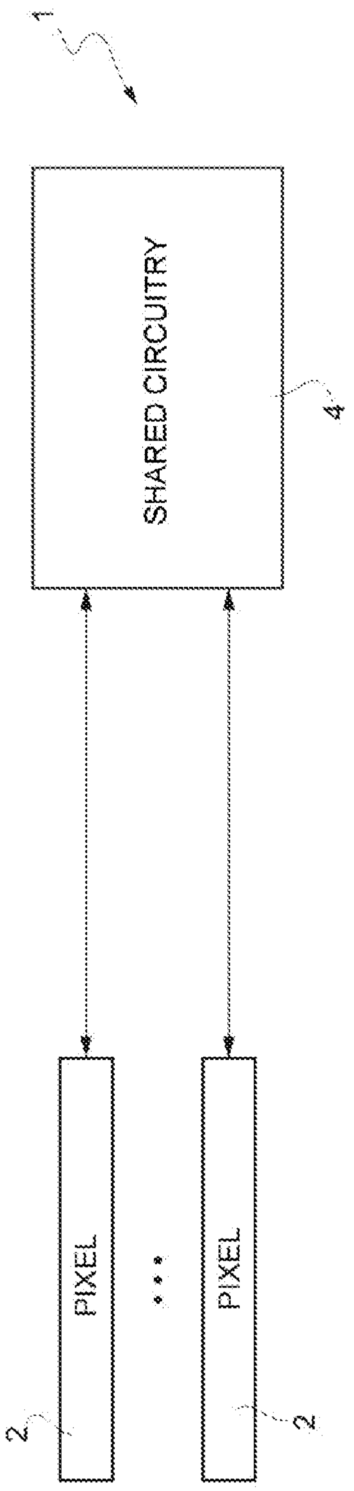
FIG. 1 shows a block diagram of a multipixel probe.
Figure 2:
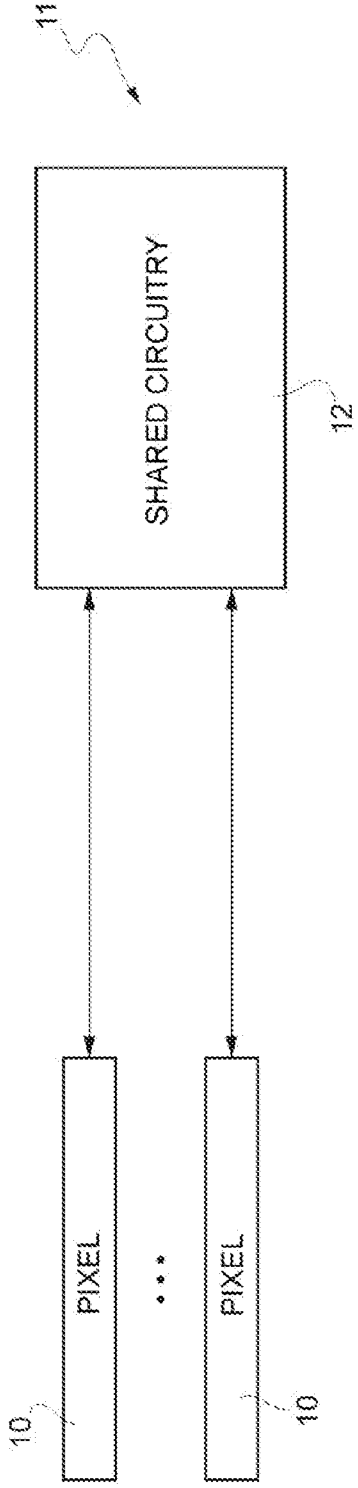
FIG. 2 shows a block diagram of a probe module including the present integrated electronic circuit.
Figure 3:
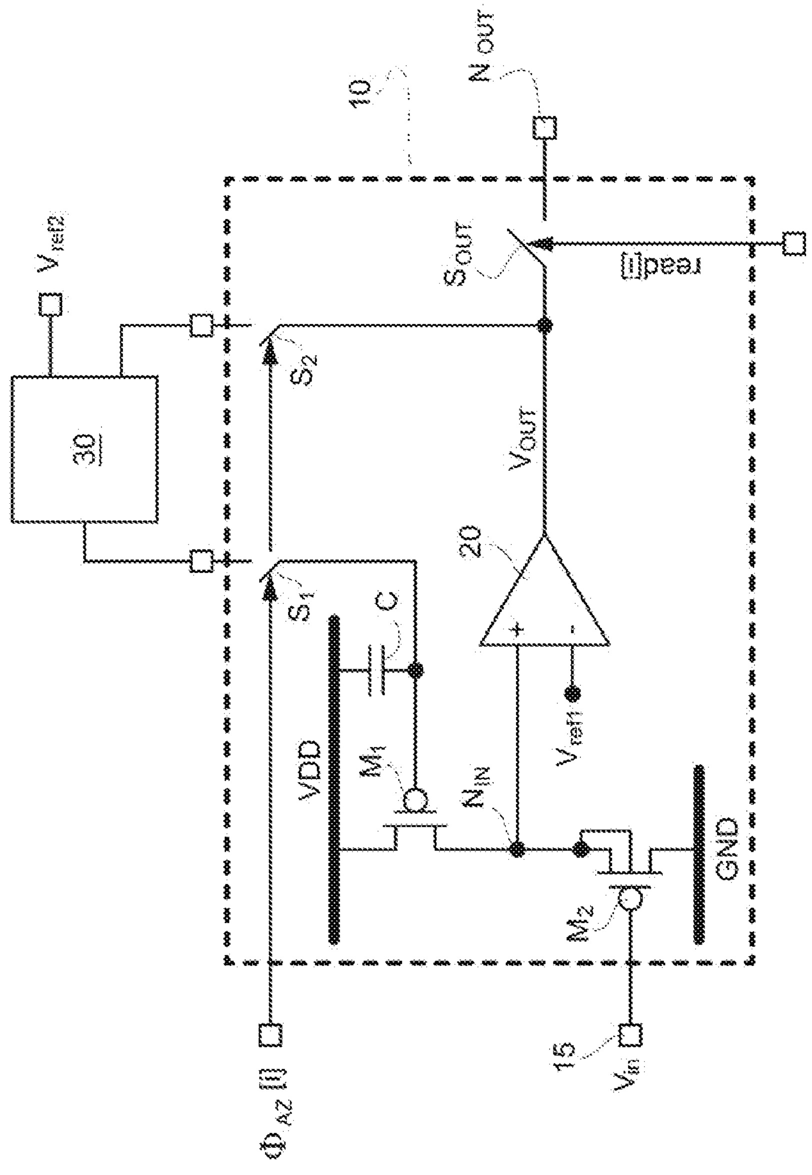
FIG. 3 shows a circuit diagram of a portion of the probe module shown in FIG. 2.

FIG. 2 shows a multi-electrode and implantable type probe module 11, which includes a shared circuitry 12 and a plurality of pixels 10 equal to each other and electrically coupled to the shared circuitry 12. For example, the pixels 10 may be thirty-two in number. One of such pixel 10 is shown in FIG. 3 and is described below.

In detail, the pixel 10 comprises a supply terminal, which in use is set to a supply voltage VDD for example equal to 1.8V, and a ground (GND). Furthermore, the pixel 10 comprises a first and a second transistor $M_1$, $M_2$, which are referred to hereinbelow as the first and second biasing transistors $M_1$, $M_2$ respectively.

The first and second biasing transistors $M_1$, $M_2$ are P-channel enhancement MOSFET transistors. Furthermore, the source terminal of the first biasing transistor $M_1$ is connected to the supply voltage VDD; the drain terminal of the first biasing transistor $M_1$ is connected to the source terminal of the second biasing transistor $M_2$, so as to form an input node $N_{IN}$. The drain terminal of the second biasing transistor $M_2$ is grounded; furthermore, and without any loss of generality, the source terminal of the second biasing transistor $M_2$ is connected to the body terminal of the second biasing transistor $M_2$.

Figure 4:
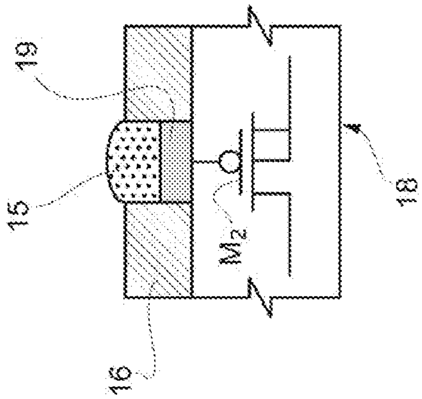
FIG. 4 schematically shows a section of a portion of a semiconductive plate.

As shown in FIG. 4, the gate terminal of the second biasing transistor $M_2$ is electrically connected to a corresponding electrode 15, which in use is placed in contact with the biological tissue to be analysed (for example, brain tissue), so that on the electrode 15 there is an input voltage $V_{in}$, which is equal to the sum of a direct voltage $V_{DC}$ and a so-called small signal voltage $V_{in}$.

As shown in FIG. 4, the electrode 15 may be formed so that it passes through a dielectric region 16 of a plate ("die") 18 in which the probe module 11 is formed, so that it contacts a metallization 19 (e.g., the upper metallization) of the plate 18, said metallization 19 being electrically connected to the gate terminal of the second biasing transistor $M_2$.

The pixel 10 further comprises a capacitor C, which has a first and a second terminal, which are respectively connected to the gate terminal of the first biasing transistor $M_1$ and to the supply voltage VDD.

Figure 5:
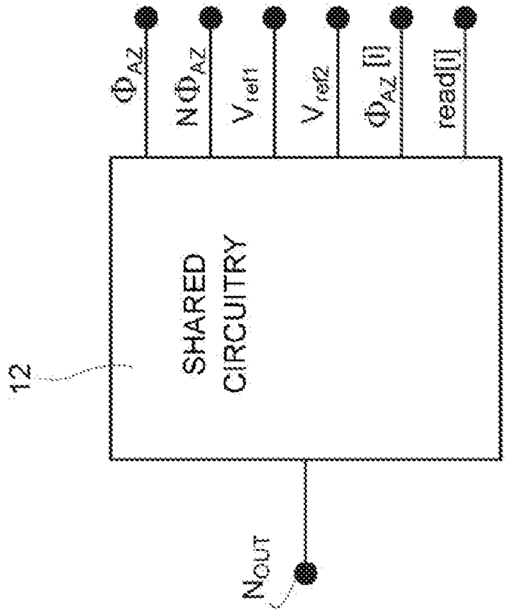
FIG. 5 shows a block diagram of a circuitry.

The pixel 10 further comprises an amplifier 20 (for example, but not limited to, of the transconductance type), the positive input terminal of which is connected to the input node $N_{IN}$, and the negative input terminal of which is connected to the shared circuitry 12, shown in FIG. 5, which sets the negative input terminal to a voltage $V_{ref1}$ (for example equal to 600 mV).

The pixel 10 furthermore comprises three switches, which are referred to hereinbelow as the first and second calibration switches $S_1$, $S_2$ and as the output switch $S_{OUT}$ respectively. As described in greater detail below, the first and second calibration switches $S_1$, $S_2$ are controlled by a signal $\Phi_{AZ}$[i], while the output switch $S_{OUT}$ is controlled by a signal read[i]. The signal $\Phi_{AZ}$[i] and the signal read[i] are generated by the shared circuitry 12, as shown in FIG. 5 and as described in greater detail below. Furthermore, the output switch $S_{OUT}$ is interposed between the output terminal of the amplifier 20 and an output node $N_{out}$, which in turn is coupled to the shared circuitry 12.

The shared circuitry 12 comprises a feedback amplifier stage 30 (shown in FIG. 3), which has a first and a second input terminal; the first input terminal is connected to the shared circuitry 12, so as to be set to a voltage $V_{ref2}$ (for example, equal to 900 mV), while the second input terminal is connected to the first terminal of the second calibration switch $S_2$, the second terminal of which is connected to the output terminal of the amplifier 20.

The feedback amplifier stage 30 has furthermore an output terminal, which is connected to a first terminal of the first calibration switch $S_1$, the second terminal of which is connected to the first terminal of the capacitor C, and therefore also to the gate terminal of the first biasing transistor $M_1$.

Figure 6:
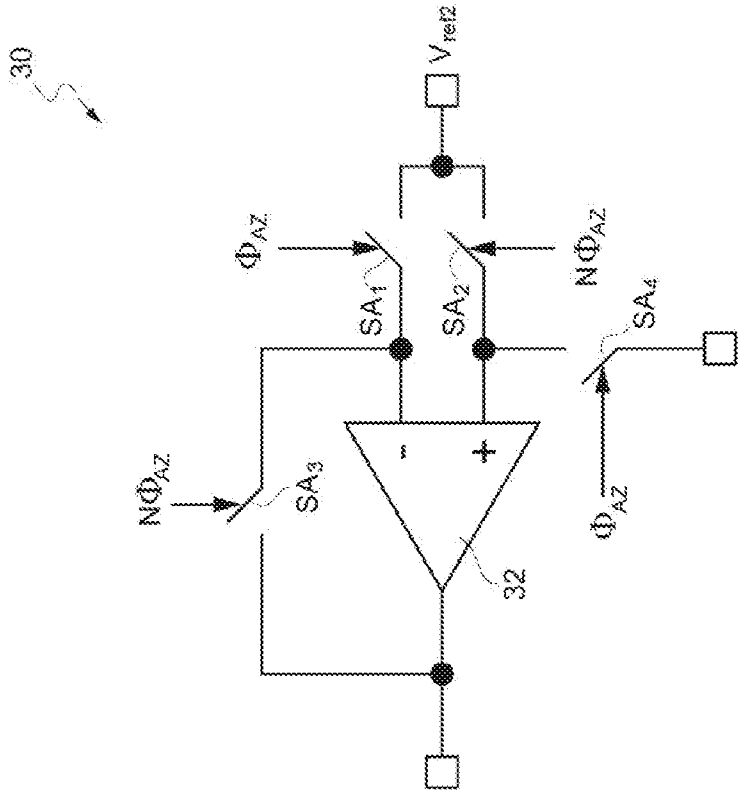
FIG. 6 shows a circuit diagram of a portion of the probe module.

In greater detail, as shown in FIG. 6, the feedback amplifier stage 30 comprises a feedback amplifier 32, example, limited to, by a formed for but not transconductance amplifier, and a first, a second, a third and a fourth additional switch $SA_1$, $SA_2$, $SA_3$, $SA_4$.

The output terminal of the feedback amplifier 32 forms the output terminal of the feedback amplifier stage 30, therefore it is connected to the first terminal of the first calibration switch $S_1$.

The first additional switch $SA_1$ is interposed between the negative input terminal of the feedback amplifier 32 and the first input terminal of the feedback amplifier stage 30, which, as mentioned above, is set to the voltage $V_{ref2}$.

The second additional switch $SA_2$ is interposed between the positive input terminal of the feedback amplifier 32 and the first input terminal of the feedback amplifier stage 30.

The third additional switch $SA_3$ is interposed between the negative input terminal of the feedback amplifier 32 and the output terminal of the feedback amplifier 32.

The fourth additional switch $SA_4$ is interposed between the positive input terminal of the feedback amplifier 32 and the second input terminal of the feedback amplifier stage 30.

Furthermore, the first and fourth additional switches $SA_1$, $SA_4$ are controlled by a signal $\Phi_{AZ}$ generated by the shared circuitry 12. In particular, the first and fourth additional switches $SA_1$, $SA_4$ are closed when the signal $\Phi_{AZ}$ is equal to '1' and are open when the signal $\Phi_{AZ}$ is equal to '0'.

The second and the third additional switches $SA_2$, $SA_4$ are controlled by a signal $N\Phi_{AZ}$ equal to the logical negation of the signal $\Phi_{AZ}$. In this way, the second and third additional switches $SA_2$, $SA_3$ are open when the signal $\Phi_{AZ}$ is equal to '1' and are closed when the signal $\Phi_{AZ}$ is equal to '0'.

In practice, the first and second biasing transistors $M_1$, $M_2$ form a so-called common drain stage, which has a unit gain and receives as input the input voltage $V_{in}$. Furthermore, as explained below, the common drain stage allows to control the direct voltage present on the positive input terminal of the amplifier 20, which provides a high gain (e.g., higher than 40 dB) over a band extending, for example, up to 4 kHz. At the output from the amplifier 20 there is an output signal $V_{OUT}$, which, when read[i]='1', is provided on the output node $N_{OUT}$, therefore it is provided to the shared circuitry 12, which reads it in a per se known way.

In greater detail, the shared circuitry 12 generates the signals $\Phi_{AZ}$ (and thus also $N\Phi_{AZ}$) and $\Phi_{AZ}$[i] so that the pixel 10 operates under different operating conditions.

Figure 7:
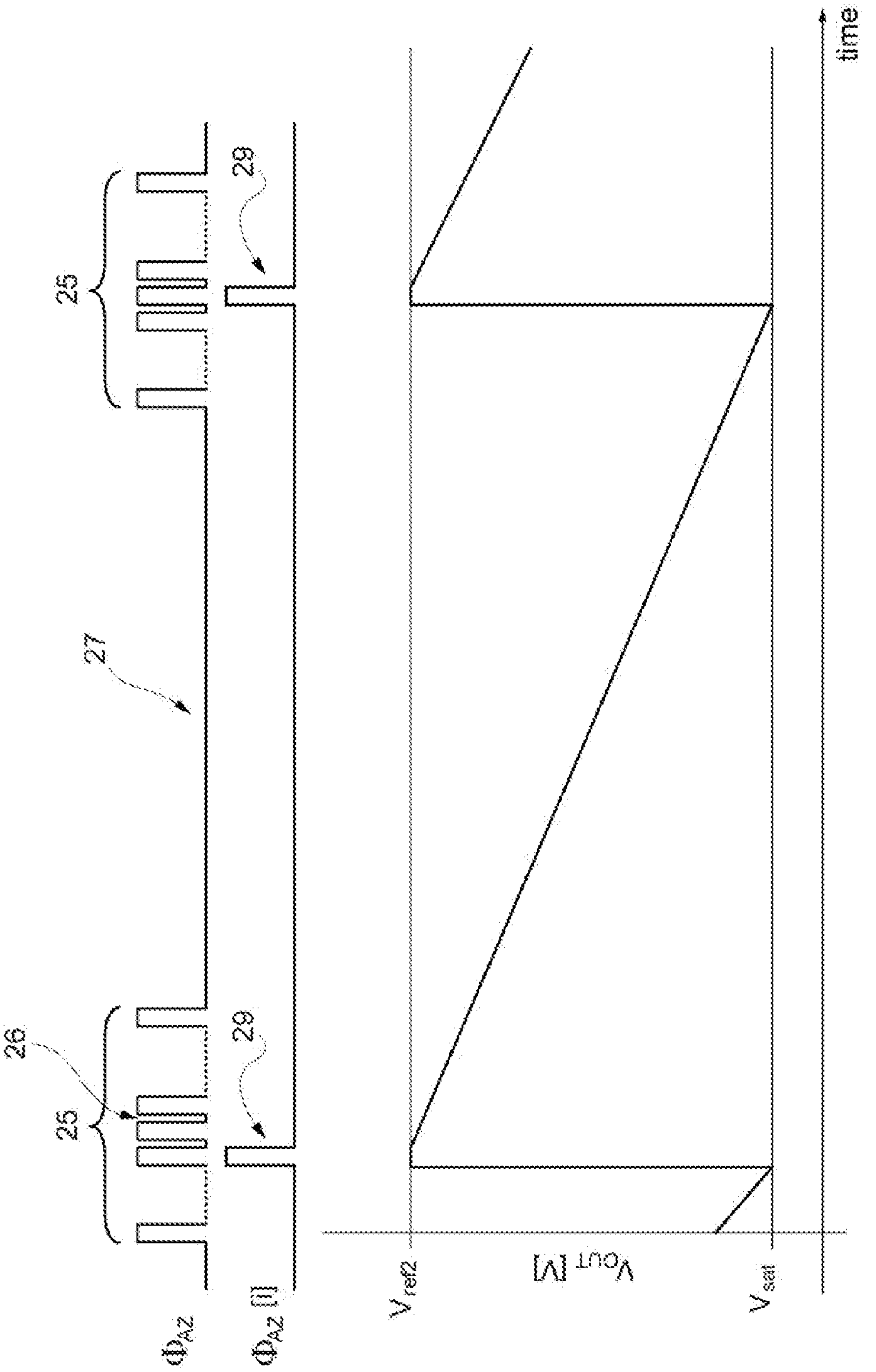
FIG. 7 shows examples of trends over time of signals.

In particular, as shown in FIG. 7, the signal $\Phi_{AZ}$ is a signal that provides for an alternation of bursts of pulses (denoted with 25) and of sensing periods (one shown in FIG. 7, where it is denoted with 27). Each pulse burst 25 comprises a number of pulses equal to the number of pixels 10.

As far as instead the signal $\Phi_{AZ}$[i] is concerned, however, it is relative to the i-th pixel 10. Furthermore, considering the i-th pixel 10, the corresponding signal $\Phi_{AZ}$[i] is generated by the shared circuitry 12 so as to be equal to '1' only when the i-th pixel 10 is selected, otherwise it is equal to '0'; furthermore, the signal $\Phi_{AZ}$[i] has a single pulse (denoted with 29) for each pulse burst 25 of the signal $\Phi_{AZ}$, said single pulse 29 being temporally aligned with a corresponding pulse of the pulse burst 25. In addition, when $\Phi_{AZ}$[i]='1', $\Phi_{AZ}$[j]='0' occurs for each j between 1 and 32, but other than i.

Figure 8:
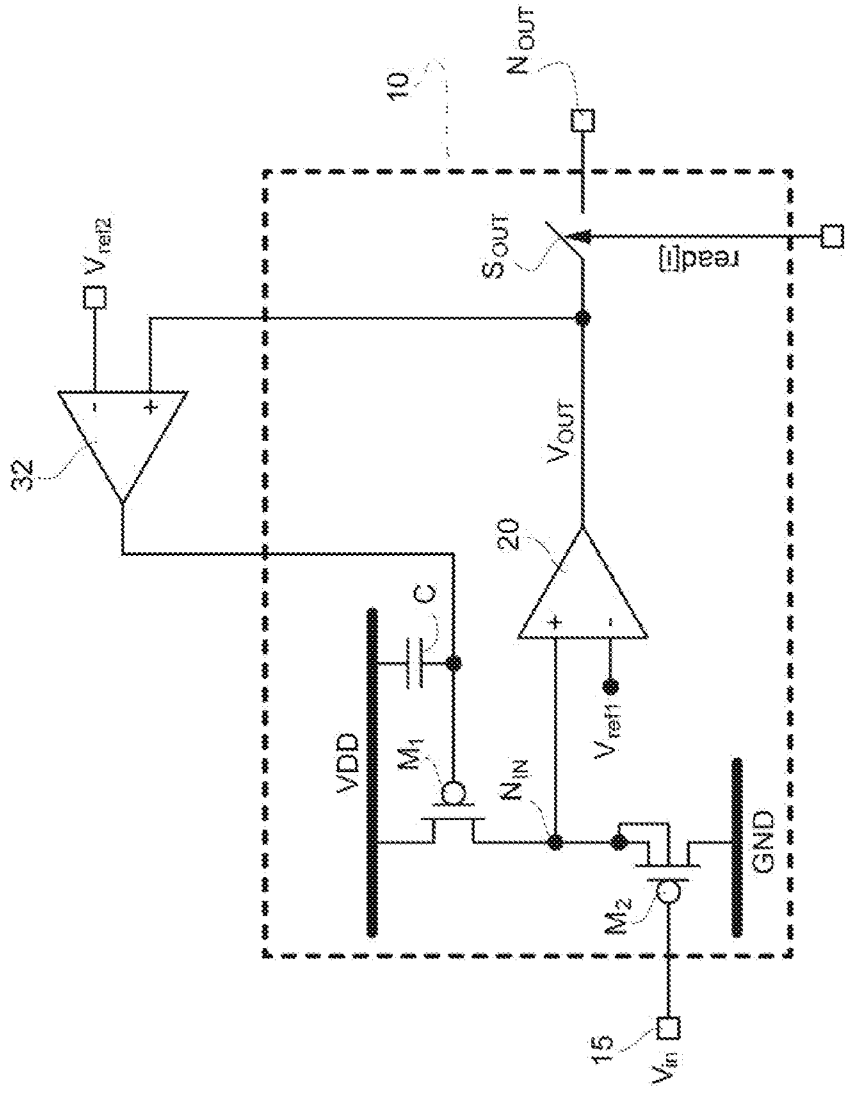
FIGS. 8 and 9 show circuit diagrams of this integrated electronic circuit, under different operating conditions.

That being said, referring again to the pixel 10 shown in FIG. 3, it can operate under a calibration condition, which is given when $\Phi_{AZ}$[i]='1', which also entails $\Phi_{AZ}$='1'; this condition is shown in FIG. 8.

In detail, the first and second calibration switches $S_1$, $S_2$ are closed, therefore the feedback amplifier 32 is coupled to the amplifier 20 and forms an autozeroing loop such that a voltage approximately equal to the voltage $V_{ref1}$ is set on the input node $N_{IN}$. In particular, the capacitor C is subject to a voltage such that the gate terminal of the first biasing transistor $M_1$ is in turn subject to a voltage such that the first biasing transistor $M_1$ injects in the input node $N_{IN}$ a biasing current $I_{bias}$. The biasing current $I_{bias}$ therefore depends on the charge stored in the capacitor C and is precisely such that the input node $N_{IN}$ is set equal to the voltage $V_{ref1}$.

Furthermore, thanks to the autozeroing loop, on the output terminal of the amplifier 20 there is a voltage approximately equal to the voltage $V_{ref2}$, as shown again in FIG. 7.

Figure 9:
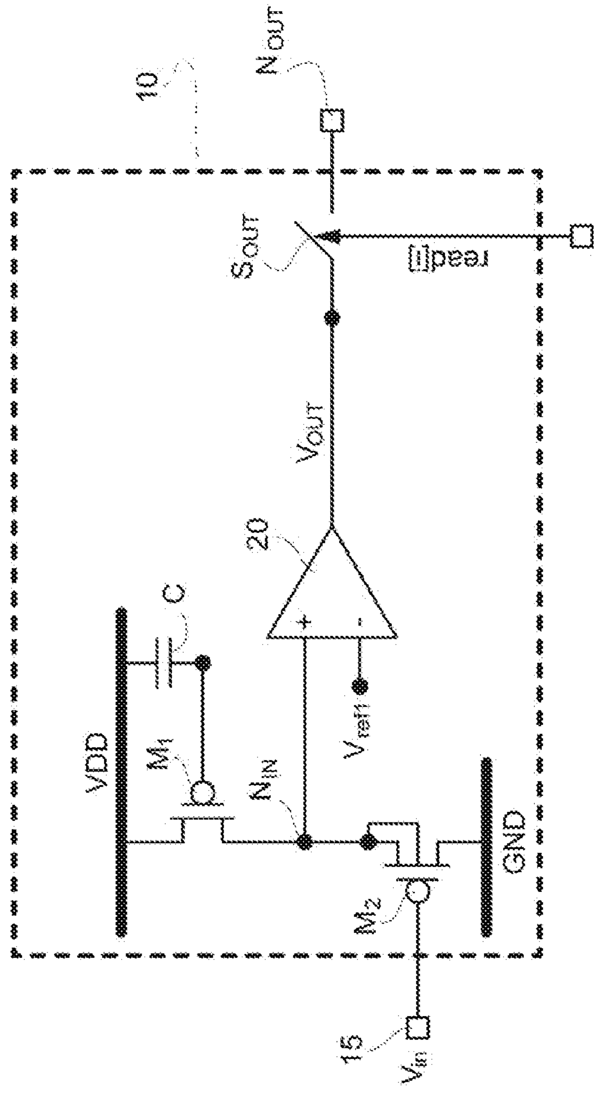

Subsequently, when the signal $\Phi_{AZ}$[i] returns to '0', the first and second calibration switches $S_1$, $S_1$ open and the pixel 10 operates under sensing conditions, shown in FIG. 9.

In practice, the feedback amplifier stage 30 is decoupled from the amplifier 20 and the autozeroing loop opens.

Ideally, the capacitor C maintains the previously stored charge, therefore the biasing current $I_{bias}$ does not vary and the input node $N_{IN}$ remains at the voltage $V_{ref1}$; consequently, the biasing of the positive input terminal of the amplifier 20 does not vary. Furthermore, the amplifier 20 operates in open loop and amplifies the input signal $V_{IN}$ present on the electrode 15, allowing a correct sensing thereof. Thus, while the pixel 10 operates under sensing conditions, the shared circuitry 12 can set read[i]='1', so that the same shared circuitry 12 can read the output signal $V_{OUT}$, which includes a direct voltage contribution equal to the voltage $V_{ref2}$ and a small signal contribution that is a function of the aforementioned small: signal voltage $V_{in}$.

In fact, due to unavoidable losses, the charge present in the capacitor C tends to reduce, causing a reduction of the biasing current $I_{bias}$ and therefore a variation (reduction) of the voltage present on the input node $N_{IN}$, with consequent reduction of the output signal $V_{OUT}$, and in particular of the direct voltage component of the latter, as shown in FIG. 7. Precisely in order to prevent this reduction from bringing the terminal at the output from the amplifier 20 so close to a limit voltage $V_{sat}$ such that correct amplification is no longer possible, the shared circuitry 12 controls each pixel 10 so as to alternate calibration conditions, in which the voltage $V_{ref1}$ is restored on the input node $N_{IN}$, at sensing conditions, in which the input signal $V_{IN}$ is read.

Furthermore, during each period of time in which the pixel 10 operates under calibration conditions, the autozeroing loop cancels the impact on the biasing of the amplifier 20 of the DC offset affecting the electrode 15, that is, it compensates for the DC offset. In this regard, thanks to the fact that the biasing current $I_{bias}$ is injected in the input node $N_{IN}$ by a single transistor (in particular, the first biasing transistor $M_1$), the interval of the DC offset values that can be compensated for (with the same voltage $V_{ref1}$) is maximized, since the biasing current $I_{bias}$ can be reduced up to a minimum value $I_{min}$ which depends on the sizing of the first and second biasing transistors $M_1$, $M_2$. In this regard, the direct voltage on the input node $N_{IN}$ is equal to the sum between the direct voltage $V_{DC}$ of the input voltage $V_{in}$ and a direct voltage $V_{DCAZ}$ set by the autozeroing loop; in the presence of high values of the direct voltage $V_{DC}$, the autozeroing loop reduces the direct voltage $V_{DCAZ}$ (to the limit, until it cancels it, if $V_{DC}=V_{ref1}$) tending to turn off the first biasing transistor $M_1$, so as to reduce the biasing current $I_{bias}$.

Figure 10:
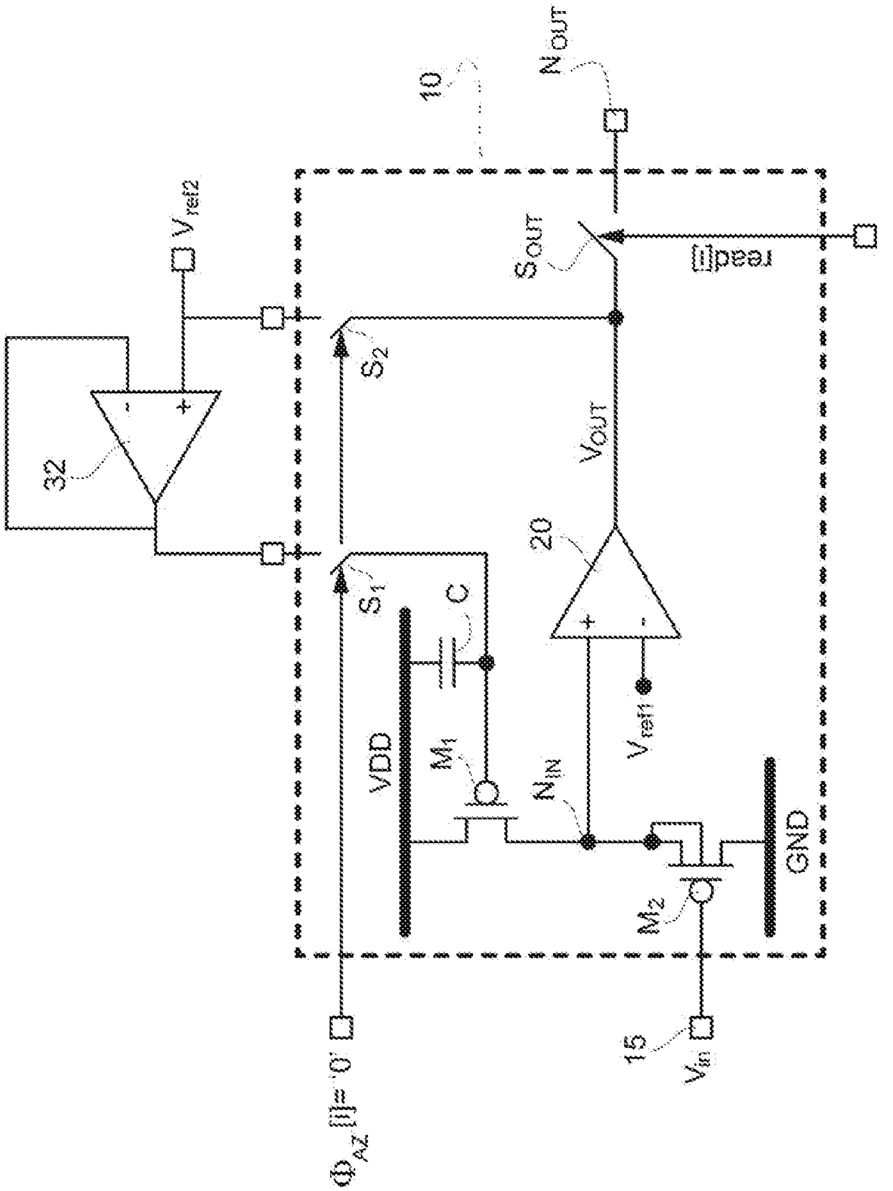
FIG. 10 shows a further circuit diagram of the probe module.

Still with reference to the biasing current $I_{bias}$, the current flowing in the second biasing transistor $M_2$ is precisely equal to the biasing current $I_{bias}$, since no current flows in the positive input terminal of the amplifier 20. With regard to the signal $\Phi_{AZ}$, when it is equal to '0', it happens that the second and third additional switches $SA_2$, $SA_3$ are closed, while the first and fourth additional switches $SA_1$, $SA_4$ are open. Consequently, as shown in FIG. 10, the feedback amplifier 32 operates as a voltage buffer and transfer the voltage $V_{ref2}$ to its own output terminal, and thus also to the first terminal of the first calibration switch $S_1$ of each pixel 10. In this way, the charge losses suffered by the capacitors C of the pixels 10 through the respective first calibration switches $S_1$ during the sensing periods 27 are reduced, because the voltage at the ends of the first calibration switches $S_1$ is controlled. The small charge losses that might occur are also reduced, considering a pulse burst 25 of the signal $\Phi_{AZ}$, during each time interval between two successive pulses of the burst (one shown in FIG. 7, where it is denoted with 26).

According to a variant, the voltages $V_{ref1}$ generated on the negative input terminals of the amplifiers 20 of the pixels 10 may vary from pixel to pixel. In other words, the shared circuitry 12 applies, on each negative input terminal of the amplifiers 20 of the pixels 10, a corresponding voltage $V_{ref1}$, with the following benefits.

In general, the autozeroing loop is capable of compensating for DC offsets in the interval $V_{ref1}\pm\Delta V$, where $\Delta V$ is proportional to the biasing current $I_{bias}$, which however is subject to an upper limit depending on the dimensions of the first and second biasing transistors $M_1$, $M_2$, as well as on the stability conditions of the autozeroing loop. Therefore, high values of the voltage $V_{ref1}$ are better suited to compensate for high values of the DC offset; on the contrary, in case the DC offset has a reduced value, the compensation is preferably obtained by adopting a reduced voltage $V_{ref1}$.

That being said, since electrodes 15 of different pixels 10 may be subject to different DC offsets, in particular in the event that the probe module 11 includes a very large array of electrodes 15, the possibility of setting, for different pixels 10, different values of the respective voltages $V_{ref1}$ (which are set on the negative input terminals of the respective amplifiers 20) allows to optimize, for each pixel 10, the compensation for the DC offset it experiences.

The advantages that the present integrated electronic circuit allows obtaining emerge clearly from the previous description. In particular, during the calibration step, the autozeroing loop including the feedback amplifier 32 allows to control the biasing current $I_{bias}$ that flows in the common drain stage and therefore allows to adjust the direct voltage present on the positive input terminal of the amplifier 20, compensating for the DC offset present in the voltage $V_{in}$. Furthermore, since the biasing current $I_{bias}$ comes from a single transistor (in this case, the first biasing transistor $M_1$), it is possible to compensate for high DC offsets, with the same voltage $V_{ref1}$.

Furthermore, the Applicant has observed that the autozeroing loop is stable, despite the wide interval of values that can be assumed by the biasing current $I_{bias}$.

It is finally clear that modifications and variants can be made to this integrated electronic circuit, without departing from the scope of the present invention, as defined by the enclosed claims.

For example, the capacitor C may be made in MIM ("metal-insulator-metal") technology or by using the parasitic capacitance present on the gate terminal of the first biasing transistor $M_1$.

For example, the negative and positive input terminals of each amplifier 20 and/or of the feedback amplifier may be reversed with respect to what is described.

Furthermore, the probe module 11 can be used together with other probe modules similar to it, so as to implement a system for recording electrical signals of biological origin with high parallelism.

Finally, the capacitor C can be grounded (GND), instead of to the supply voltage VDD.

The invention claimed is:

1. An integrated electronic circuit for an implantable probe module, comprising a number of pixel circuits each including:

an electrode configured to contact a biological tissue;

a biasing stage comprising a capacitor and a first transistor having a respective control terminal and a respective first conduction terminal, which are respectively coupled to the capacitor and to an input node, the first transistor being configured to inject in the input node a biasing current that depends upon the charge of the capacitor;

a second transistor, which has a respective control terminal and a respective first conduction terminal, which are respectively coupled to the electrode and to the input node;

an amplifier having a first input terminal, configured to be set to a corresponding first reference voltage, and a second input terminal, which is coupled to the input node;

said integrated electronic circuit further comprising:

a feedback stage electrically controllable so as to be alternatively coupled or decoupled from the biasing stage and from the amplifier of each pixel circuit, said feedback stage being configured to form, when coupled to the biasing stage and to the amplifier of a pixel circuit, an autozeroing loop that charges the corresponding capacitor so that the corresponding biasing current is such that on the corresponding input node a voltage substantially equal to the corresponding first reference voltage is present;

wherein the feedback stage has a first input terminal, configured to be set to a second reference voltage, a second input terminal and a respective output terminal, said feedback stage further comprising a feedback amplifier, the output terminal of which is coupled to the output terminal of the feedback stage; and wherein each pixel circuit further comprises a respective first switch, which is controllable so as to couple/decouple the corresponding capacitor to the output terminal of the feedback stage, and a respective second switch, which is controllable so as to couple/decouple the output terminal of the corresponding amplifier to the second input terminal of the feedback stage; and wherein the feedback stage is electrically controllable so as to operate alternatively in a first configuration, in which a first and a second input terminal of the feedback amplifier are respectively coupled to the first and to the second input terminals of the feedback stage, and in a second configuration, wherein the first and the second input terminals of the feedback amplifier are respectively coupled to the output terminal of the feedback amplifier and to the first input terminal of the feedback stage (30), in such a way that the feedback amplifier operates as a voltage follower and transfers the second reference voltage to the output terminal of the feedback stage.

2. The integrated electronic circuit according to claim 1, wherein each pixel circuit is configured so that the respective second transistor is traversed by the same biasing current injected by the corresponding first transistor.

3. The integrated electronic circuit according to claim 1, wherein the feedback amplifier is a transconductance amplifier.

4. The integrated electronic circuit according to claim 1, further comprising a control circuitry configured to control the first and second switches of the pixel circuits so as to couple the feedback stage to one pixel circuit at a time, said control circuitry being further configured to control the feedback stage so that, when said feedback stage is coupled to a pixel circuit, the feedback stage operates in the first configuration; said control circuitry being further configured to alternate first periods of time, in which the pixel circuits are individually coupled, in succession, to the feedback stage, with second periods of time, wherein the feedback stage is decoupled from the pixel circuits and operates in the second configuration.

5. The integrated electronic circuit according to claim 1, wherein the second transistor of each pixel circuit has a respective second conduction terminal, which is set to a first reference potential; and wherein the first transistor of each pixel circuit has a respective second conduction terminal, which is set to a second reference potential; and wherein the capacitor of each pixel circuit has a respective first terminal, set to the first or the second reference potential, and a respective second terminal, coupled to the control terminal of the corresponding first transistor.

6. The integrated electronic circuit according to claim 1, wherein the first and second transistors of each pixel circuit are P-channel enhancement MOSFET transistors.

7. The integrated electronic circuit according to claim 1, further comprising a biasing circuitry coupled to the first input terminals of the amplifiers of the pixel circuits and configured to set, on each of said input terminals, a corresponding first reference voltage.

8. The integrated electronic circuit according to claim 1, wherein the amplifier of each pixel circuit is configured to generate an output signal on its own output terminal; said integrated electronic circuit further comprising a reading circuit couplable in an electrically controllable manner to the pixel circuits, so as to read the respective output signals.

9. The integrated electronic circuit according to claim 1, wherein the amplifier of each pixel circuit is a transconductance amplifier.

* * * * *